United States Patent
Friberg

(10) Patent No.: US 7,212,937 B2
(45) Date of Patent: May 1, 2007

(54) GAS FLOW MEASURING DEVICE

(75) Inventor: Harri Friberg, Buchs (CH)

(73) Assignee: imt medical ag, Liechtenstein (LI)

( * ) Notice: Subject to any disclaimer, the term of this patent is extended or adjusted under 35 U.S.C. 154(b) by 0 days.

(21) Appl. No.: 10/534,558

(22) PCT Filed: Oct. 22, 2003

(86) PCT No.: PCT/IB03/04653

§ 371 (c)(1),
(2), (4) Date: Nov. 18, 2005

(87) PCT Pub. No.: WO2004/046661

PCT Pub. Date: Jun. 3, 2004

(65) Prior Publication Data

US 2006/0144163 A1 Jul. 6, 2006

(30) Foreign Application Priority Data

Nov. 20, 2002 (CH) .................... 2010/02

(51) Int. Cl.
*G01F 1/12* (2006.01)
(52) U.S. Cl. .................... 702/100

(58) Field of Classification Search .......... 702/100
See application file for complete search history.

(56) References Cited

U.S. PATENT DOCUMENTS

| 5,179,958 | A | 1/1993 | Mault |
| 6,090,049 | A | 7/2000 | Cha |
| 6,368,287 | B1 | 4/2002 | Hadas |
| 6,468,222 | B1 | 10/2002 | Mault et al. |
| 6,683,679 | B2 * | 1/2004 | Belenkii ............ 356/28.5 |
| 2003/0065275 | A1 * | 4/2003 | Mault et al. ........ 600/531 |
| 2003/0171887 | A1 * | 9/2003 | Cha et al. ............ 702/100 |

FOREIGN PATENT DOCUMENTS

WO   WO0147417   7/2001

* cited by examiner

*Primary Examiner*—John Barlow
*Assistant Examiner*—Demetrius R. Pretlow
(74) *Attorney, Agent, or Firm*—Kaplan Gilman Gibson & Dernier LLP

(57) ABSTRACT

The invention relates to a device for the exact measurement of gases with a plurality of sensors which are evaluated by means of a microcontroller so that high accuracy of measurement is obtained independently of the environmental conditions, which are also measured.

8 Claims, 2 Drawing Sheets

Block diagram

Fig. 1: Block diagram
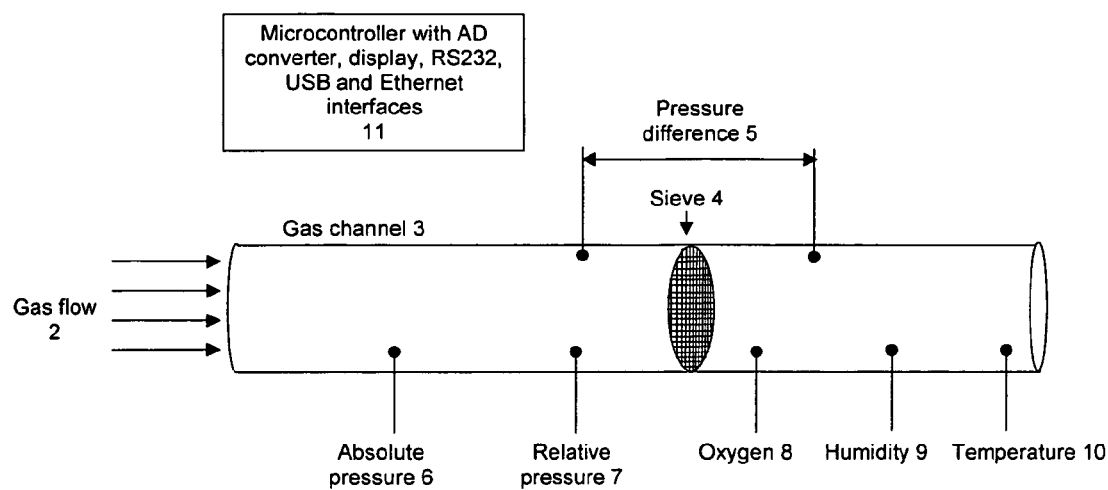
Fig. 2: Gas block in FlowAnalyser measuring device
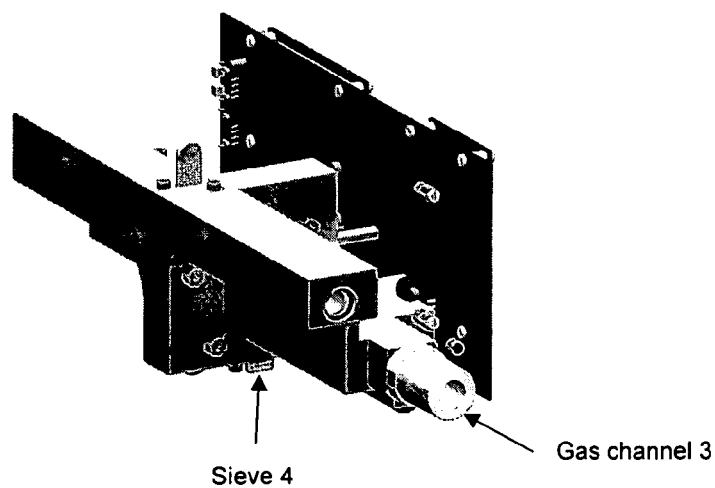

Fig. 3: Detail of the front panel
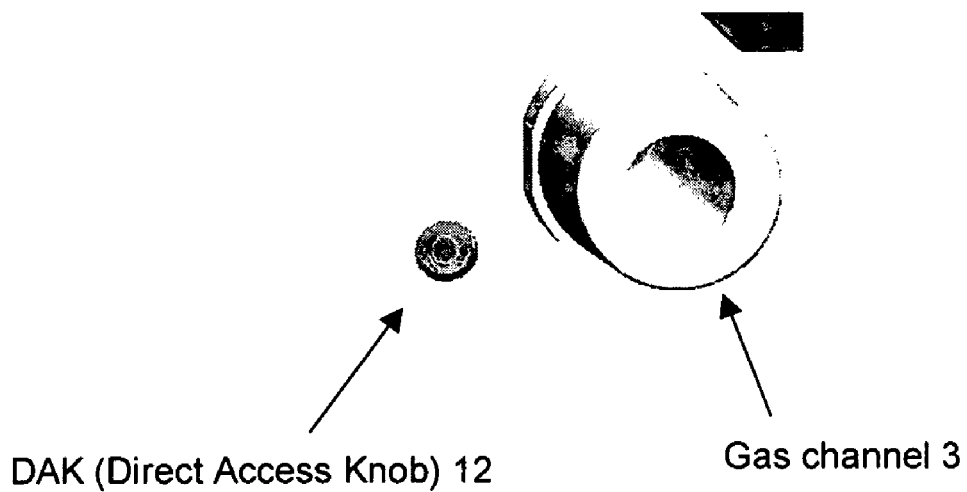
DAK (Direct Access Knob) 12      Gas channel 3
Fig.4 Front view of overall device
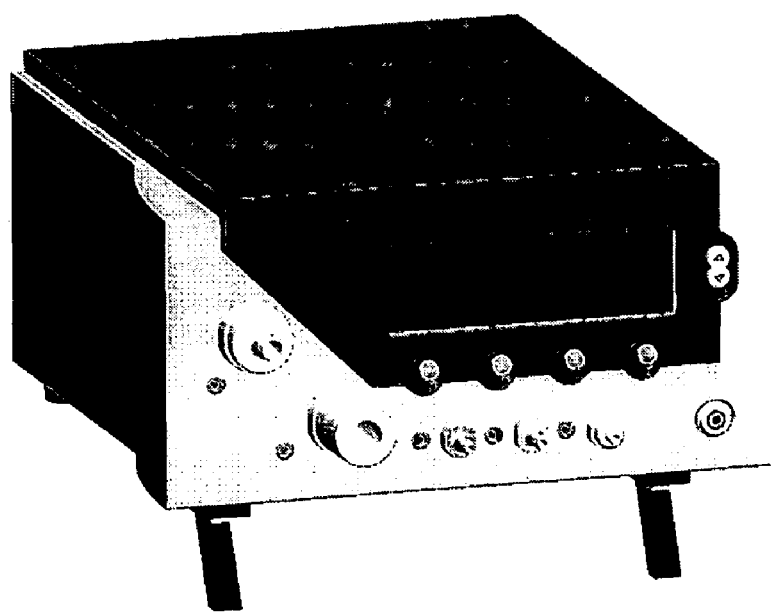

GAS FLOW MEASURING DEVICE

BACKGROUND

Stationary and portable gas flow and pressure measuring devices are required for the calibration, production and standardization of devices of all types. Devices available to date have the disadvantage that the gas flow measurements are influenced by the environmental conditions, and miscalibrations therefore occur. This is very problematic especially in the case of medical devices, such as respiratory and anesthesia devices. Since the devices are used worldwide, miscalibrations also result from incorrect operation of the devices.

There have to date been several efforts to perform an exact gas measurement. The following measuring principles are known:

Ultrasound

Two combined ultrasonic transmitter/receiver units which are arranged at an angle to the inflow direction. These send an ultrasound pulse at regular intervals and wait for the reception of the pulse of the other transmitter. If ultrasound waves cover a defined distance s in a known medium they require for this purpose a time t dependent on their propagation velocity. The propagation velocity of a wave is thus dependent on the transit time of the signal from one transmitter/receiver to the other.

Volume Counter with Measuring Vanes

A vane wheel is caused to rotate so that its speed is proportional to the mean flow rate.

Wind Pressure Method

The medium flows through a nozzle or aperture. The cross-section is narrowed, which accelerates the flow rate. In order to avoid vortex formation, venturi nozzles are generally used. The mass flow is then calculated from the pressure difference across the nozzle.

Laminar Flow Elements

Like the wind pressure method, laminar flow elements are based on the fact that the flow can be calculated from a pressure difference. In contrast thereto, however, the flow is linear relative to the measured pressure difference. In medicine, the laminar flow elements are known as pneumotachographs.

Hot-Wire Anenometer

A wire or a surface is heated to a temperature which is above the ambient temperature. Molecules which strike this surface and then fly off again absorb kinetic energy there. The heat loss of the heated surface is proportional to the temperature difference between the heated surface and the environment and to the number of molecules striking per unit time.

All these known structures are at their limits, and the exactness of the measurement is restricted. Particularly in the area of medicine, however, it was intended to increase the accuracy further. This is the object of the invention. It is intended to improve the accuracy of gas flow measurement.

The measurement properties of the individual methods differ and, depending on the application, one or other measuring device—optionally optimized—is used.

Particularly in the case of special devices in the area of medicine, such as, for example, respiratory devices, anesthesia devices, etc., however, a very wide range of applications are present in a device, so that it was necessary to date to measure using a plurality of measuring devices, or to be satisfied with a certain accuracy of measurement—for example for standardization or monitoring purposes.

SUMMARY

The invention therefore relates to a device for exact flow measurement of gases independently of the environmental conditions, such as temperature, humidity, type of gas, oxygen concentration and ambient pressure. It is intended to make as few compromises as possible and to be able to measure a large number of very different applications with high accuracy.

Furthermore, the operation should be as easy as possible in order to avoid incorrect manipulations. The measurement can be capable of being carried out under any environmental conditions as far as possible with the same accuracy.

These objects are achieved by the Applicant's portable measuring device "FlowAnalyser".

BRIEF DESCRIPTION OF THE FIGURES

For the purposes of illustrating the various aspects of the invention, there are shown in the drawings forms that are presently preferred, it being understood, however, that the invention is not limited to the precise arrangements and instrumentalities shown.

FIG. 1 is a block diagram of a gas measurement device in accordance with one or more embodiments of the present invention;

FIG. 2 is a perspective view of an embodiment of a gas block of the device of FIG. 1;

FIG. 3 is a detailed view of a front panel of a gas measurement device in accordance with one or more embodiments of the present invention; and FIG. 4 is a perspective view of an embodiment of a gas measurement device in accordance with one or more embodiments of the present invention.

DETAILED DESCRIPTION

With reference to FIGS. 1–4, the measuring device according to the invention comprises a device (1) for the measurement of gases with a gas channel (3), with a sieve (4) and with a plurality of different sensors (5), (6), (7), (8), (9), (10), a plurality of sensors (5–10) which can exactly measure both humid and dry gases being installed in the gas channel (3) through which the gas stream to be measured flows, and all sensors being connected to a computer which compares the individual measured values of the individual sensors with one another and comprises a program by means of which a consolidated measured value for the gas actually flowing through can be specified from various measured values. Certain sensors serve for determining the environmental conditions.

The gas flow 2 flows through the gas channel 3 and through the sieve 4 which is mounted in the middle of the gas channel 3. This sieve can be easily changed and, like the other components, is shown only schematically. The gas channel 3 is formed so as to result in a laminar flow of the gas flowing through. A large number of sensors 5–10 having different measuring tasks and/or different measuring ranges is present in the gas channel. A microcontroller 11, which is not shown in detail, processes the different measured values in order to be able to determine a measured flow value which is as exact as possible for the respective application under the respective environmental conditions.

The sensor values of the sensors 5–10 are thus read in by the microcontroller 11 preferably provided as a module and are converted into an exact gas flow.

In the device according to the invention, in particular the environmental influences of humidity, absolute pressure, temperature and oxygen concentration are taken into account in the calculation of the gas flow in the computer, for example a microcontroller (11), so that the measurement is always exactly correct under all environmental conditions.

According to a particular embodiment of the invention, the gas channel (3) is in the form of a compact block in which all sensors are directly integrated. The use of tubes between the sensors is avoided according to the invention.

According to a particular embodiment of the invention, the gas channel (3) and the sieve (4) are designed so that, independently of the direction of flow, a laminar gas flow results, and that bidirectional gas measurement is thus possible as a special feature. This is advantageous, for example, in respiratory devices since it is possible thereby to measure both the gas mixture delivered to the patient and the gas mixture delivered back by the patient, which permits conclusions about the patient's condition.

According to a further development of the invention, a Direct Access Knob (DAK) for direct access to help and measured values is arranged on the front panel of the device, adjacent to the gas channel (3), which direct access knob is connected by the computer to a display and permits immediate display of current measured values or help functions on this display.

The invention is not limited to certain sensors or sensor types. Rather, the person skilled in the art can choose from the known sensor types, for example according to the introduction to the description.

FIG. 4 shows a preferred overall design of the device according to the invention.

LIST OF REFERENCE NUMERALS

Part of the Disclosure Together with Drawing
1 Gas flow measuring device
2 Gas flow
3 Gas channel
4 Sieve
5 Differential pressure sensor
6 Absolute pressure sensor
7 Relative pressure sensor
8 Oxygen sensor
9 Humidity sensor
10 Temperature sensor
11 Microcontroller system
12 Direct Access Knob (DAK)

The invention claimed is:

1. A device for the measurement of gas flows, comprising:
a gas channel;
sensors arranged in the gas channel, wherein the gas channel is in the form of a compact block and groups of different sensors with different measured values or measuring ranges are integrated without tubes directly in the gas channel and are installed in such a way that both humid and dry gases can be measured; and
a computer or microcontroller where, in the operating state, individual measured values of the different sensors are compared with one another by the computer or microcontroller so that a resultant measured value is specified from the individual measured values,
wherein two groups of sensors are provided, on the one hand pressure sensors for measurement of the pressure difference across a measuring resistance arranged in the gas channel and in the form of a sieve, of an absolute or ambient pressure and of a relative pressure in the gas channel, and, on the other hand, sensors for measurement of humidity, temperature and oxygen concentration, and the computer or microcontroller is provided with program parameters for calculating the gas flow which take into account environmental influences determined by the individual sensors, including at least one of humidity, ambient pressure, temperature and oxygen concentration, and relative pressure in the gas channel, so that an interfering effect of the environmental conditions on the measured values is compensated.

2. The device as claimed in claim 1, wherein the sensors are screwed into the block from outside and can be removed therefrom or changed.

3. The device as claimed in claim 1, wherein the gas channel and the measuring resistance or the sieve are designed in such a way that a laminar gas flow results in both directions of flow and hence bidirectional gas measurement without influencing the measured value is possible.

4. The device as claimed in claim 1, wherein at least one of:
a direct access knob (DAK) for direct access to help functions and measured values exists on a front panel of the device; and
the direct access knob (DAK) for direct access to help functions and measured values exists adjacent to the gas channel.

5. The device as claimed in claim 4, wherein the direct access knob triggers a display or the delivery of actual values of different—optionally selectable—parameters to a display.

6. The device as claimed in claim 2, wherein the gas channel and the measuring resistance or the sieve are designed in such a way that a laminar gas flow results in both directions of flow and hence bidirectional gas measurement without influencing of the measured value is possible.

7. The device as claimed in claim 2, wherein at least one of:
a direct access knob (DAK) for direct access to help functions and measured values exists on a front panel of the device; and
the direct access knob (DAK) for direct access to help functions and measured values exists adjacent to the gas channel.

8. The device as claimed in claim 3, wherein at least one of:
a direct access knob (DAK) for direct access to help functions and measured values exists on a front panel of the device; and
the direct access knob (DAK) for direct access to help functions and measured values exists adjacent to the gas channel.

* * * * *

UNITED STATES PATENT AND TRADEMARK OFFICE
Certificate

Patent No. 7,212,937 B2  Patented: May 1, 2007

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Harri Friberg, Buchs (CH); and Jakob Däscher, Buchs (CH).

Signed and Sealed this Twentieth Day of May 2008.

JOHN E. BARLOW
*Supervisory Patent Examiner*
Art Unit 2863